(12) United States Patent
Hunter et al.

(10) Patent No.: US 10,444,180 B1
(45) Date of Patent: Oct. 15, 2019

(54) POLYMER ELECTROLYTE-BASED SENSORS

(75) Inventors: Gary W Hunter, Oberlin, OH (US); Jennifer C Xu, Olmsted Township, OH (US); Chung-Chiun Liu, Cleveland Heights, OH (US)

(73) Assignee: United States of America as Represented by the Administrator of National Aeronautics and Space Administration, Washington, DC (US)

( * ) Notice: Subject to any disclaimer, the term of this patent is extended or adjusted under 35 U.S.C. 154(b) by 388 days.

(21) Appl. No.: 13/552,760

(22) Filed: Jul. 19, 2012

Related U.S. Application Data

(60) Provisional application No. 61/510,755, filed on Jul. 22, 2011.

(51) Int. Cl.
*G01N 27/406* (2006.01)
*G01N 27/407* (2006.01)

(52) U.S. Cl.
CPC ......... *G01N 27/406* (2013.01); *G01N 27/407* (2013.01)

(58) Field of Classification Search
CPC ..... G01N 27/404–4045; G01N 27/406; G01N 27/409; G01N 27/41
USPC ............ 204/410, 414, 418, 419, 421–424; 73/23.31, 23.32
See application file for complete search history.

(56) References Cited

U.S. PATENT DOCUMENTS

| | | | | |
|---|---|---|---|---|
| 4,125,374 A | * | 11/1978 | Bode et al. | 436/137 |
| 5,322,602 A | * | 6/1994 | Razaq | 205/788 |
| 5,387,329 A | * | 2/1995 | Foos | C08F 220/14 204/403.06 |
| 5,521,101 A | * | 5/1996 | Saini et al. | 205/777.5 |
| 2005/0034985 A1 | * | 2/2005 | Zamanzadeh et al. | 204/424 |
| 2005/0034987 A1 | * | 2/2005 | Zhou et al. | 204/426 |
| 2007/0015893 A1 | * | 1/2007 | Hakuta et al. | 528/34 |
| 2007/0054170 A1 | * | 3/2007 | Isenberg | 429/33 |
| 2007/0102294 A1 | * | 5/2007 | Dorisio Deininger | G01N 27/4071 204/421 |
| 2010/0266926 A1 | * | 10/2010 | Hirashige | H01B 1/122 429/479 |
| 2011/0079523 A1 | * | 4/2011 | Offenbacher et al. | 205/793 |

\* cited by examiner

*Primary Examiner* — Gurpreet Kaur
(74) *Attorney, Agent, or Firm* — Robert H. Earp, III; William M. Johnson

(57) ABSTRACT

A polymer electrolyte-based sensor is disclosed. The sensor includes a conductive polymer electrolyte film including water-retaining components. The water-retaining components facilitate operational conductivity of the conductive polymer electrolyte film in lower humidity environments than would be possible without the water-retaining components.

20 Claims, 5 Drawing Sheets

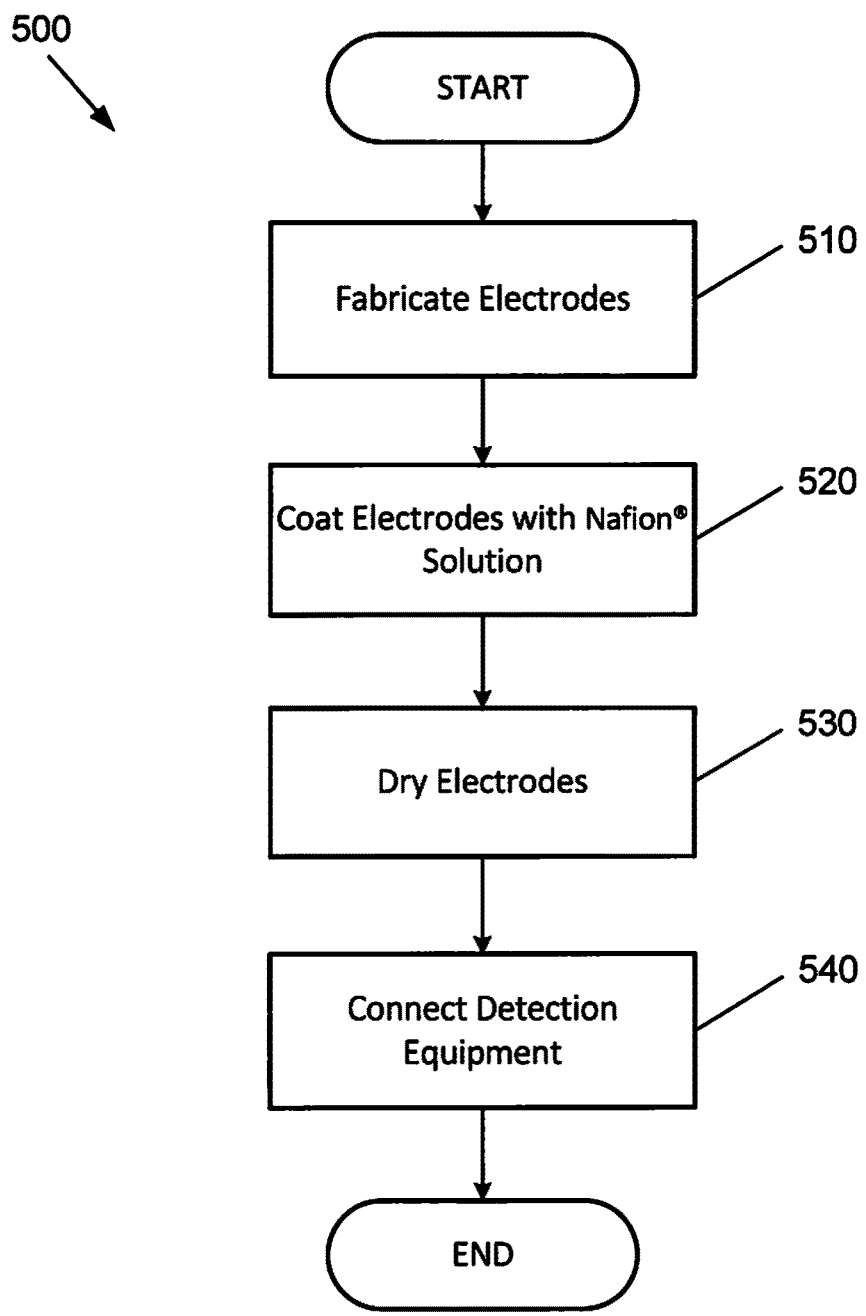

POLYMER ELECTROLYTE-BASED SENSORS

CROSS REFERENCE TO RELATED APPLICATIONS

This application is a non-provisional of, and claims priority to, U.S. Provisional Patent Application Ser. No. 61/510,755, filed Jul. 22, 2011, the subject matter of which is hereby incorporated by reference in its entirety.

ORIGIN OF THE INVENTION

The invention described herein was made by employees of the United States Government and may be manufactured and used by or for the Government for Government purposes without the payment of any royalties thereon or therefore.

The invention described herein was also made in the performance of work under a NASA contract and is subject to the provisions of Section 305 of the National Aeronautics and Space Action of 1958, Public Law 85-568 (72 Stat. 435; 42 U.S.C. 2457).

FIELD

The present invention generally pertains to sensors, and more specifically, to polymer electrolyte-based sensors for environmental, safety, and personal monitoring applications.

BACKGROUND

Sensing of gas concentrations is important for various terrestrial and space applications. Some conventional ambient temperature oxygen sensors are optical-based, including expensive and complicated instrumentation. These types of systems can also be susceptible to humidity effects and cross-interference. Other conventional ambient temperature oxygen sensors are based on conventional electrochemical cells, which include aqueous electrolytes. Both types of sensors are not packaging-friendly and the electrochemical cells are susceptible to leaking, particularly in space or variable pressure applications. These types of sensors are also difficult to miniaturize.

A few conventional solid state oxygen sensors are high temperature electrolyte-based. The electrolyte needs to be heated to a high temperature (e.g., 600° C. or more) to achieve practical levels of sensitivity. This is due to the intrinsic properties of the solid electrolyte sensing materials. Such conventional sensors also have considerable power consumption requirements. In an effort to reduce the power consumption of such sensors, NASA Glenn Research Center and Case Western Reserve University have successfully developed a high temperature oxygen microsensor using Yttria-Stabilized Zirconia ("YSZ") as a solid state electrolyte sensing material. The sensor has the advantages of a wide detection range, small size, easy batch fabrication, relatively low cost, and low power consumption. However, although such a design significantly reduces power consumption due to its micro size, the sensors still need to be heated to a high temperature (e.g., 600° C.) to achieve a practical sensitivity to oxygen. These high temperature sensors are still not suitable for some space applications, such as those in close contact with astronauts, and can limit the battery operation of the sensor system in portable units.

In view of these disadvantages, in oxygen detecting microsensors, use of a Nafion® film may be beneficial. A significant advantage of Nafion®-based sensors is that they can detect oxygen at ambient temperature, which can significantly save power consumption required for heating. In another approach that can decrease power consumption, the system can be operated in a potentiometric mode. As such, no power needs to be applied for the sensor to operate. Rather, only an electrometer, or potentiometric meter, is needed for measuring the voltage changes between a working electrode and a reference electrode under different gas environments. Accordingly, the power consumption is extremely low, making such sensors particularly useful for many applications.

However, in lower humidity environments, the ability of Nafion® to operate effectively as a detecting medium breaks down. For example, in a desert environment, Nafion® film could gradually lose conductivity when its moisture content as a whole drops below 20%. This is because Nation® is more conductive in higher humidity environments and less conductive in lower humidity environments since the presence of sufficient water within the electrolyte material is critical for its effective operation. While Nafion® may work reasonably well for oxygen detection in environments with humidity, such as within a spacesuit or standard ambient humidity environments, Nafion® is suboptimal for less humid environments, such as higher temperature environments with little or no humidity. Accordingly, a low power sensor that operates in environments with varying humidity may be beneficial.

SUMMARY

Certain embodiments of the present invention may be implemented and provide solutions to the problems and needs in the art that have not yet been fully solved by conventional sensors. For example, certain embodiments of the present invention use a Nafion® film doped with a water-retaining material to facilitate effective sensor operation in lower humidity environments.

In one embodiment of the present invention, an apparatus includes a conductive polymer electrolyte film including water-retaining components. The water-retaining components facilitate operational conductivity of the conductive polymer electrolyte film in lower humidity environments than would be possible without the water-retaining components.

In another embodiment of the present invention, a sensor includes a conductive polymer electrolyte film including water-retaining components. The sensor also includes a working electrode and reference electrode, each at least partially coated with the conductive polymer electrolyte film.

In yet another embodiment of the present invention, a method for producing a sensor includes at least partially coating a working electrode and a reference electrode with a conductive polymer electrolyte film including water-retaining components. The method also includes drying the working electrode and the reference electrode to form a thin layer of the conductive polymer electrolyte film over the electrodes such that the film retains a predetermined amount of water.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 5 is a flowchart illustrating a process for producing a sensor, according to an embodiment of the present invention.

DETAILED DESCRIPTION OF THE EMBODIMENTS

Figure 1:
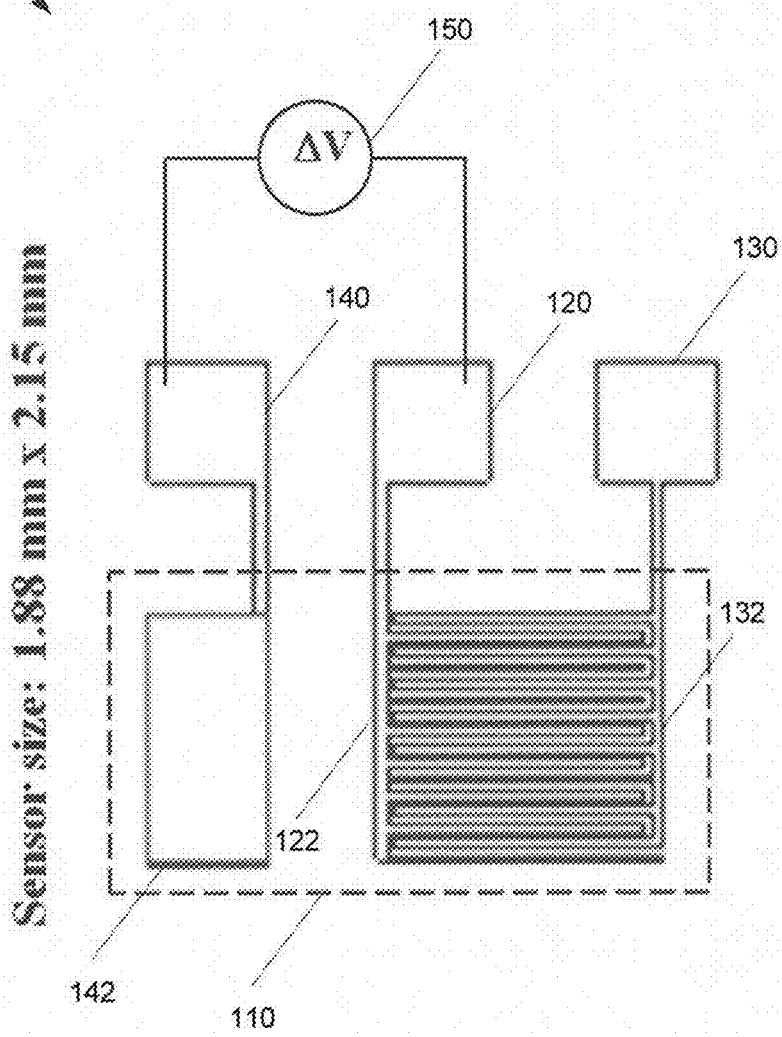
FIG. 1 illustrates a potentiometric oxygen sensor, according to an embodiment of the present invention.

Some embodiments of the present invention pertain to a novel ambient temperature oxygen ($O_2$) microsensor based on a Nafion® polymer electrolyte that is suitable for applications such as long-term environmental monitoring, portable detection of oxygen by a handheld unit, and for extra-vehicular activity ("EVA") spacesuit oxygen monitoring. Although Nafion® is described with respect to many embodiments herein, other conductive polymer electrolyte materials that depend on moisture for operation may also be used, such as Hyflon®, Flemion®, Aciplex®, sulfonated polyether ether ketone, sulfonated polyarylene ether sulfone, polystyrene sulfonic acid, sulfonated polymides, and polybenzimidizole ("PBI"). In some embodiments, the conducting polymer Nafion® may be mixed with water-retaining components, such as certain salts. Such embodiments are well-suited to operation in humid environments, overcoming issues faced by optical sensors. For instance, many embodiments are well-suited for ambient temperature oxygen detection in a humid EVA spacesuit environment where the air has a relatively high moisture content due to the breath of an astronaut. Such embodiments are also well-suited for lower humidity environments, such as atmospheres with high temperatures and low humidity.

As discussed above, in lower humidity environments, the ability of Nafion® to operate effectively as a detecting medium breaks down due to lower conductivity without sufficient water being present. However, due to the water retaining capabilities of the doped Nafion®, some embodiments may be particularly well-suited to sustained and consistent lower humidity operation that conventional Nafion® sensors are not capable of. The water retaining component, such as a salt, holds and homogeneously distributes water molecules in the Nafion® film, increasing hydration.

Many embodiments can operate at room temperature in a potentiometric mode that measures voltage differences between working and reference electrodes in different gases. As such, no power needs to be applied for the sensor to operate. Rather, only an electrometer, or potentiometer, is needed for measuring the voltage changes between a working electrode and a reference electrode under different gas environments. Accordingly, the power consumption is extremely low, making such sensors useful for many applications.

Many embodiments may have extremely low power consumption (i.e., no heating or voltage are applied to the sensor and only a potentiometric meter is used), small size, low cost, are simple to batch fabricate and be high in sensor yield, and are easy to use. Due to these properties, such embodiments may be particularly beneficial for aerospace and terrestrial applications, including fire detection, fuel leak detection, space environment monitoring, and potential EVA applications. Some embodiments may also be fabricated using thin film technologies. Other embodiments can be amperometric and allow the setting of a voltage and the measurement of a current flow. In these embodiments, the detection of other species besides oxygen may be enabled by selective control of the voltage.

Potentiometric and Amperometric Sensor Configurations

FIG. 1 illustrates a potentiometric oxygen sensor 100, according to an embodiment of the present invention. In this embodiment, potentiometric oxygen sensor 100 has a size of 1.88 mm by 2.15 mm. As such, the sensor is quite small and portable. Potentiometric oxygen sensor 100 includes a Nafion® film 110 with water-retaining components. Nafion® film 110 is used as an electrolyte material. However, the potentiometric oxygen sensor can be made smaller by changing the working electrode from a many-finger configuration to a single finger configuration, similar to reference electrode 130.

Nafion® film 110 contains a working electrode 120, a counter electrode 130, and a reference electrode 140. While counter electrode 130 is shown here, in some embodiments, only a working electrode and a reference electrode are present. Working electrode 120 has working interdigitated fingers 122 and counter electrode 130 has counter interdigitated fingers 132. The interdigitated fingers typically do not physically touch. While not used here, counter electrode 130 could be used for amperometric operation, such as in FIG. 2. In certain embodiments, the interdigitated finger width and the spacing between the interdigitated fingers may be 30 µm, for example. Reference electrode 140 has a single finger 142. A potentiometer 150 is connected to working electrode 120 and reference electrode 140. Per the above, counter electrode 130 is not used in this embodiment, and working electrode 120 and counter electrode 130 need not have multiple fingers in some embodiments. For instance, the electrodes may only have a single finger, and/or may have different numbers of fingers with respect to one another. Potentiometer 150 detects voltage differences between working electrode 120 and reference electrode 140.

Metal/metal oxide is used for reference electrodes, and the metal oxide portion should be on top of the metal portion. A noble metal, such as platinum, silver, palladium, ruthenium, etc., may be preferable. For example, palladium/palladium oxide (Pd/PdO) on top of base electrode ruthenium (Ru) or platinum (Pt) may be used, or Pd, Ru, or Pt may be used as the base electrode metal, then the reference electrode surface may be coated with PdO, $RuO_2$, or PtO to form Pd/PdO, $Ru/RuO_2$, or Pt/PtO, respectively. Other metal/metal oxide combinations, such as copper/copper oxide (Cu/CuO) and nickel/nickel oxide (Ni/NiO), can also be used as reference electrodes, preferably through using a noble metal as the base electrode material, which means depositing a noble metal for working, counter, and reference first, then depositing another metal/metal oxide combination on top of the reference electrode. However, non-noble metals, such as titanium, nickel, niobium, or tantalum, may be used for the reference electrode in some embodiments. By using this architecture, the need to seal the reference electrode and use a reference gas is eliminated. As a result, the sensor structure is simplified and miniaturization is more easily realized. For example, in a reference electrode with Pd/PdO, in operation, $2PdO+4e+4H^+ \leftrightarrow 2Pd+2H_2O$. In the working electrode, $O_2+4e+4H^+ \leftrightarrow +2H_2O$. Thus, the overall reaction is $2Pd+O_2 \leftrightarrow 2PdO$.

The combination of interdigitated electrodes with a unique solid reference electrode enables the sensor to be flexible for both potentiometric and amperometric operation modes, depending on the implementation. The interdigitated electrodes can achieve high current output when used in the amperometric mode and the solid reference electrode structure may be fabricated with metal/metal oxide components, such as palladium/palladium oxide (Pd/PdO), ruthenium/ruthenium oxide (Ru/RuO$_2$), platinum/platinum oxide (Pt/PtO), or any other suitable metal/metal oxide combination.

Figure 2:
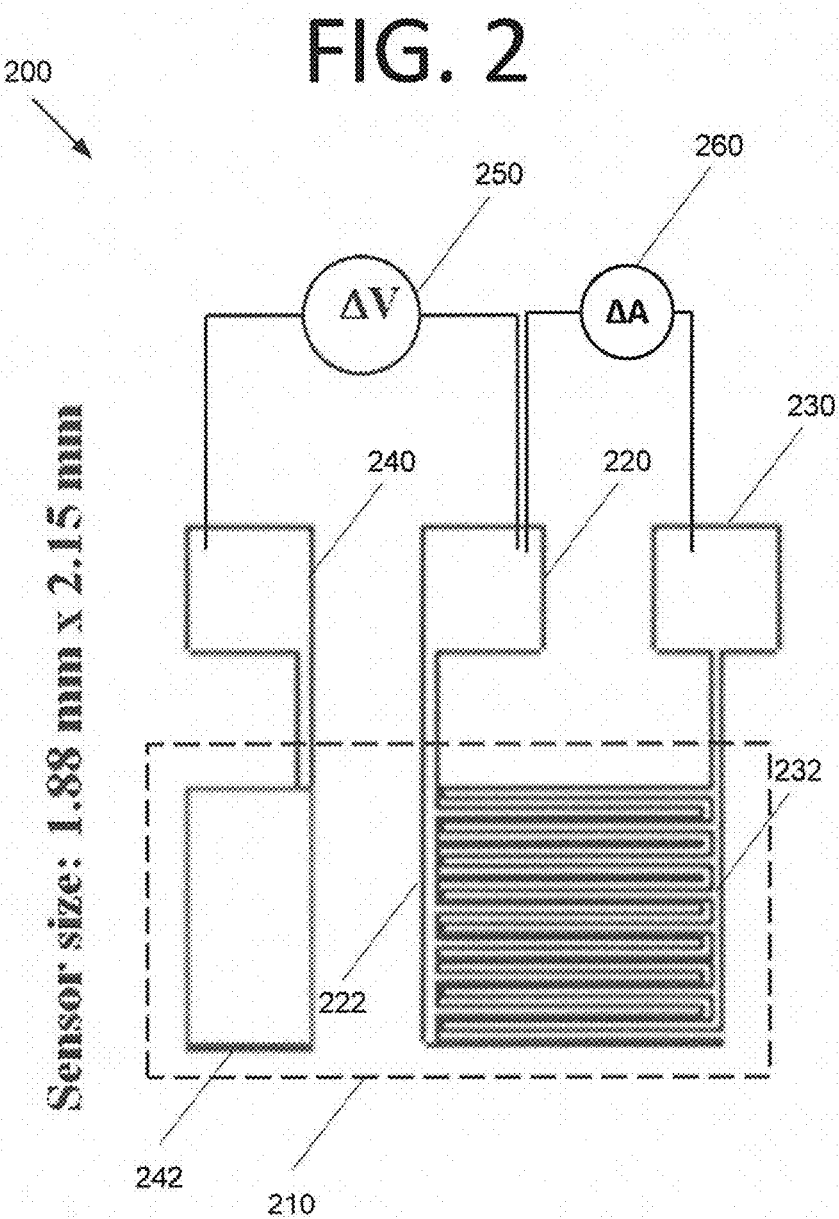
FIG. 2 illustrates a combined potentiometric/amperometric oxygen sensor, according to an embodiment of the present invention.

FIG. 2 illustrates a combined potentiometric/amperometric oxygen sensor 200, according to an embodiment of the present invention. In this embodiment, a Nafion® film 210 with water-retaining components is used as an electrolyte material. Nafion® film 210 contains a working electrode 220, a counter electrode 230, and a reference electrode 240. Working electrode 220 has working interdigitated fingers 222 and counter electrode 230 has counter interdigitated fingers 232. Reference electrode 240 has a single finger 242.

A potentiometer 250 is connected to working electrode 220 and reference electrode 240. An amperometer 260 measures current between working electrode 220 and counter electrode 230. When sensor 200 is operated under potentiometric mode, only reference electrode 240 and working electrode 220 are generally connected. The voltage difference measured by potentiometer 250 between reference electrode 240 and working electrode 220. However, when sensor 200 is operated under amperometric mode, two types of setups may be involved. The first setup is a simple two electrode system, in which a voltage is applied between working electrode 220 and counter electrode 230, and the resulting current is measured by amperometer 260. In this first setup, no reference electrode is needed. The second setup is a three electrode system, in which a voltage is applied between working electrode 220 and reference electrode 240, and the current output is measured between working electrode 220 and counter electrode 230 by amperometer 260. The three electrode system usually gives more accurate measurements, but typically requires an electrochemical analyzer or instrumentation for the measurements. The connection is also shown in FIG. 2. A voltage is applied between reference electrode 240 and working electrode 220, and the current output is measured by amperometer 260 between working electrode 220 and counter electrode 230.

The embodiment of FIG. 2 is capable of both potentiometric and amperometric operation. However, in some embodiments, only an amperometer is used. Potentiometric modes of operation use less power and provide less stress on the electrode films due to no current flow, so they may be more desirable for certain applications.

Figure 3:
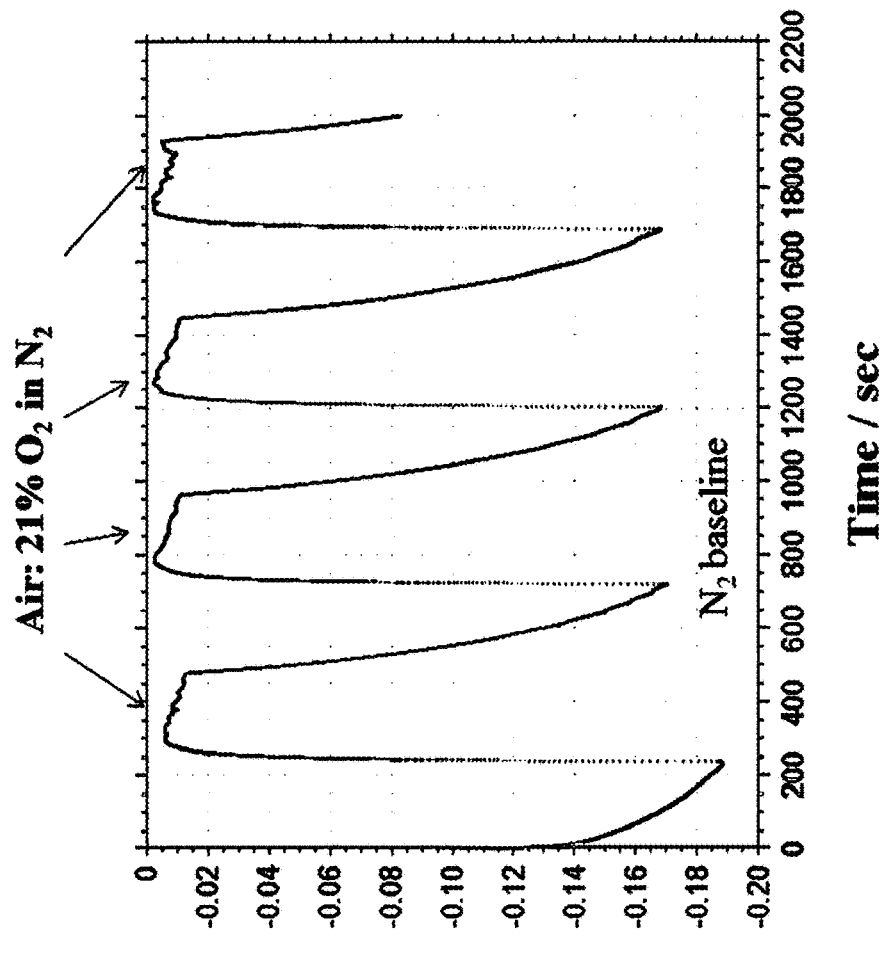
FIG. 3 is a graph 300 illustrating potentiometric operation of sensor responses to 21% oxygen in nitrogen, according to an embodiment of the present invention

FIG. 3 is a graph 300 illustrating potentiometric operation of sensor responses to 21% oxygen in nitrogen, according to an embodiment of the present invention. Data is shown for 2,000 seconds. The voltage potential approaches zero when the O$_2$ concentration is 21%.

Figure 4:
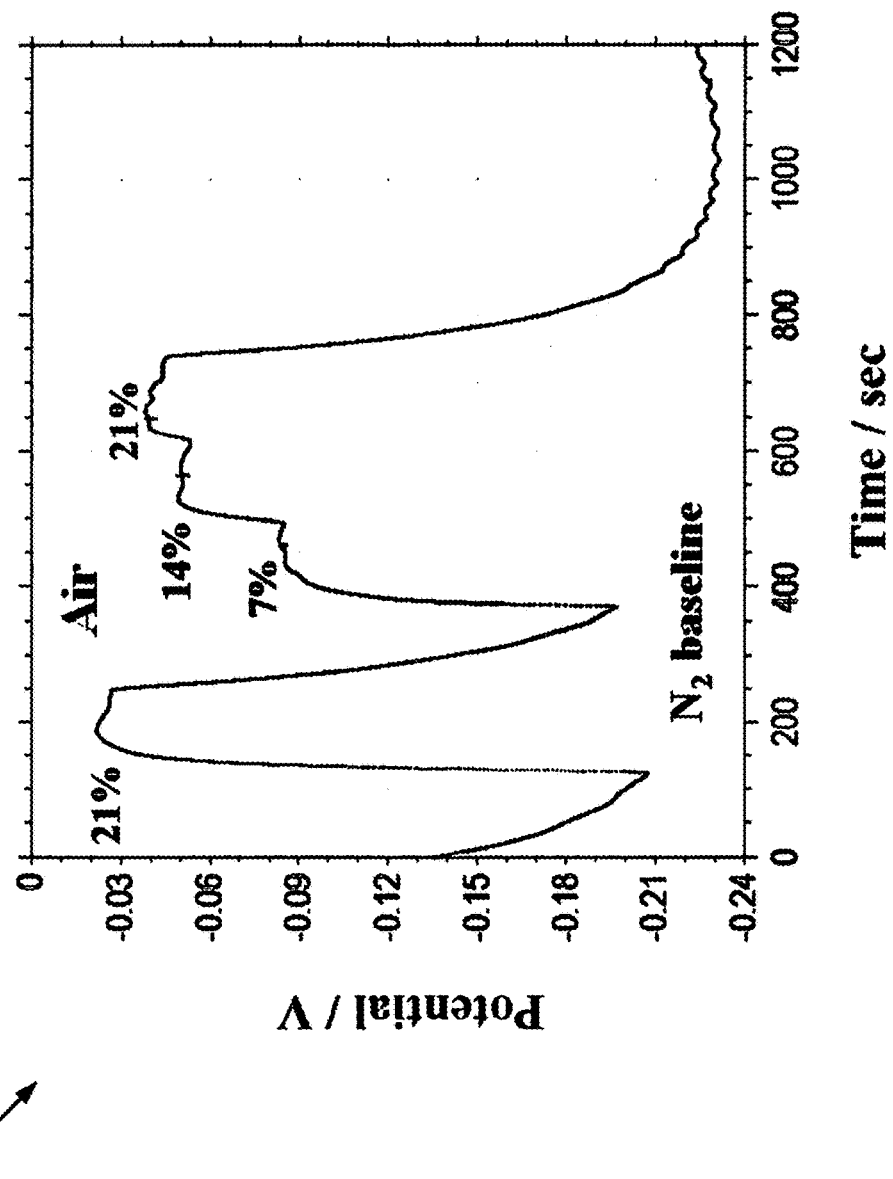
FIG. 4 is a graph 400 illustrating potentiometric operation of sensor responses in oxygen concentrations from 7% to 21% with a nitrogen baseline, according to an embodiment of the present invention.

FIG. 4 is a graph 400 illustrating potentiometric operation of sensor responses in oxygen concentrations from 7% to 21% with a nitrogen baseline, according to an embodiment of the present invention. Data is shown for 1,200 seconds. The voltage potential is approximately −0.08V when the O$_2$ concentration is 7%, −0.05V when the O$_2$ concentration is 14%, and between −0.02V and −0.04V when the O$_2$ concentration is 21%.

Water-Retaining Components

In order to retain water more effectively, water retention components are added to the Nafion® film. Suitable components include salts such as copper (II) sulfate pentahydrate (CuSO$_4$.5H$_2$O), ZnSO$_4$.7H$_2$O, MgSO$_4$.7H$_2$O, NiSO$_4$.7H$_2$O, and ethylene glycol. Per the above, the conductivity of Nafion® film depends on the moisture level in the film. Without one or more water retention components, the sensor could dry out in low humidity environments. The idea behind adding water retaining components such as CuSO$_4$.5H$_2$O or other suitable salts is that they always contain water molecules in their structures at room temperature. For instance, for each CuSO$_4$ molecule, there are 5 H$_2$O molecules. CuSO$_4$ is water-soluble and mixes well with a Nafion® solution. CuSO$_4$ molecules and their corresponding H$_2$O molecules can be distributed homogeneously in the solution and in the Nafion® film.

Per the above, the other water retention component in some embodiments is ethylene glycol. The addition of ethylene glycol increases the water retention of the Nafion® film due to its OH— groups. The OH— groups can also provide more sites for protons to move around. Other organics may also be added to the solution, such as glycerol, diethylene glycol, triethylene glycol, and propylene glycol. Presence of organics provides extra water holding capability and extra sites in the Nafion® film to promote proton (H$^+$) mobility, and thus improving Nafion® film conductivity and sensor performance. Thus, the conductivity of the Nafion® film is improved. Other suitable water-retaining materials include diol, triol, and polyol with small molecules; salts that are neutral, water soluble, and contain water molecules at ambient temperature; and all suitable organics or salts that are hygroscopic in nature.

Fabrication and Sensor Production

A microfabrication process may be used to create micro-sized sensor electrodes of some embodiments. The application of photolithography and sputtering processes to fabricate sensor electrodes enables the sensor to have a small size. The electrodes of FIGS. 1 and 2, for instance, would be difficult to fabricate via other processes due to their small size. The electrodes may be batch fabricated with low cost, high yield, and robust structure.

FIG. 5 is a flowchart 500 illustrating a process for producing a sensor, according to an embodiment of the present invention. The process begins with fabricating the working and reference sensor electrodes at 510 using photolithography and sputtering processes. The working electrode may have interdigitated fingers, particularly if amperometric operation is to be included.

Next, the sensor electrodes are coated at 520 with a Nafion® solution mixed with CuSO$_4$.5H$_2$O and ethylene glycol. The bodies of the sensor electrodes are coated. The sensor electrodes are then air dried at 530 to form a thin layer of Nafion® film that retains a certain amount of water. This approach keeps the Nafion® from drying out completely such that it remains conductive. Finally, detection equipment, such as a potentiometer, an amperometer, or both, is connected to the appropriate electrode fingers at 540. The electrodes may also be placed on a substrate made from any suitable material, such as Al$_2$O$_3$ or SiO$_2$. The process then ends with a complete and functioning sensor.

Some embodiments of the present invention are directed to a sensor having a Nafion® film with water-retaining components. The water-retaining components may include $CuSO_4.5H_2O$ and ethylene glycol, for example. A potentiometer and/or an amperometer are operably connected to appropriate fingers of working and/or reference electrodes to detect changes in voltage or current, providing information about gas content in an environment.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus, comprising:
a solid conductive polymer electrolyte film comprising:
a conductive polymer electrolyte material dependent upon moisture for conductivity;
a salt that always contains water molecules in its structure at room temperature, the salt homogeneously distributed within and throughout the conductive polymer electrolyte material to control water retention;
water molecules homogeneously distributed within and throughout the conductive polymer electrolyte material; and
a working electrode and a reference electrode both disposed on a surface of a substrate, wherein at least parts of both the working electrode and the counter electrode are contained between the surface and the solid conductive polymer electrolyte film, wherein the substrate is constructed from a material that is different than the solid conductive polymer electrolyte film;
wherein the solid conductive polymer electrolyte film does not require continuous hydration to facilitate operational conductivity in lower humidity environments.

2. The apparatus of claim 1, further comprising:
a potentiometeric sensor operably connected to the working electrode and the reference electrode, wherein the potentiometeric sensor is configured to detect voltage potential between the working electrode and the reference electrode.

3. The apparatus of claim 2, wherein the reference electrode comprises a metal and a metal oxide.

4. The apparatus of claim 3, wherein the metal comprises a noble metal, titanium, nickel, niobium, or tantalum.

5. The apparatus of claim 1, further comprising:
a counter electrode also disposed on the surface; and
an amperometer operably connected to the working electrode and the counter electrode, wherein
the amperometer is configured to detect current between the working electrode and the counter electrode when a voltage is applied between the working electrode and the counter electrode.

6. The apparatus of claim 1, wherein the salt comprises $CuSO_4.5H_2O$, $ZnSO_4.7H_2O$, $Cu(NO_3)_2.5H_2O$, $CuCl_2.2H_2O$, $MgSO_4.7H_2O$, or $NiSO_4.7H_2O$.

7. The apparatus of claim 1, wherein the solid conductive polymer electrolyte film further comprises one or more of ethylene glycol, glycerol, diethylene glycol, triethylene glycol, propylene glycol, diol, triol, and polyol.

8. The apparatus of claim 1, wherein the solid conductive polymer electrolyte film comprises sulfonated polyether ether ketone, sulfonated polyarylene ether sulfone, polystyrene sulfonic acid, sulfonated polymides, or polybenzimidizole.

9. A sensor, comprising:
a solid conductive polymer electrolyte film comprising:
a conductive polymer electrolyte material dependent upon moisture for conductivity;
a salt that always contains water molecules in its structure at room temperature, the salt homogeneously distributed within and throughout the conductive polymer electrolyte material to control water retention;
water molecules homogeneously distributed within and throughout the conductive polymer electrolyte material;
wherein the solid conductive polymer electrolyte film does not require continuous hydration to facilitate operational conductivity in lower humidity environments; and a working electrode, a counter electrode, and a reference electrode each disposed on a surface of a substrate, wherein parts of the working electrode, the counter electrode, and the reference electrode are covered by the solid conductive polymer electrolyte film such that the parts of the working electrode, the counter electrode, and the reference electrode are disposed between the surface and the solid conductive polymer electrolyte film, wherein the substrate is constructed from a material that is different than the solid conductive polymer electrolyte film.

10. The sensor of claim 9, further comprising:
a potentiometer operably connected to the working electrode and the reference electrode, wherein the potentiometer is configured to detect voltage potential between the working electrode and the reference electrode.

11. The sensor of claim 9, wherein the reference electrode comprises a metal and a metal oxide.

12. The sensor of claim 11, wherein the metal comprises a noble metal, titanium, nickel, niobium, or tantalum.

13. The sensor of claim 9, further comprising:
an amperometer operably connected to the working electrode and a counter electrode, wherein the amperometer is configured to detect current between the working electrode and the counter electrode when a voltage is applied between the electrodes.

14. The sensor of claim 9, wherein the salt comprises $CuSO_4.5H_2O$, $ZnSO_4.7H_2O$, $Cu(NO_3)_2.5H_2O$, $CuCl_2.2H_2O$, $MgSO_4.7H_2O$, or $NiSO_4.7H_2O$.

15. The sensor of claim 9, wherein the solid conductive polymer electrolyte film further comprises one or more of ethylene glycol, glycerol, diethylene glycol, triethylene glycol, propylene glycol, diol, triol, and polyol.

16. The sensor of claim 9, wherein the conductive polymer electrolyte film comprises sulfonated polyether ether ketone, sulfonated polyarylene ether sulfone, polystyrene sulfonic acid, sulfonated polymides, or polybenzimidizole.

17. The apparatus of claim 1, wherein the working electrode and the reference electrode are constructed from a noble metal layer disposed on the surface of the substrate, wherein the reference electrode further comprises a stack disposed on the noble metal layer, wherein the stack comprises a first layer constructed of a first metal and a second layer constructed of a metal oxide of the first metal.

18. The apparatus of claim 17, wherein the first metal comprises one of Pd, Ru, Cu, or Ni.

19. The sensor of claim 9, wherein the working electrode, the counter electrode, and the reference electrode are constructed from a noble metal layer disposed on the surface of the substrate, wherein the reference electrode further comprises a stack disposed on the noble metal layer, wherein the stack comprises a first layer constructed of a first metal and a second layer constructed of a metal oxide of the first metal.

20. The sensor of claim 19, wherein the first metal comprises one of Pd, Ru, Cu, or Ni.

* * * * *